United States Patent [19]

Simonovitch

[11] 4,317,824

[45] Mar. 2, 1982

[54] DERIVATIVES OF QUINOXALINE-1,4-DIOXIDES

[75] Inventor: Chaim Simonovitch, Rischon Letzion, Israel

[73] Assignee: Abic, Ltd., Israel

[21] Appl. No.: 806,303

[22] Filed: Jun. 13, 1977

[30] Foreign Application Priority Data

Jun. 24, 1976 [IL] Israel .......................... 49902

[51] Int. Cl.³ .................. C07D 401/06; C07D 241/44; A61K 31/495; C07D 417/06
[52] U.S. Cl. ..................................... 424/250; 426/532; 260/243.3; 544/62; 544/116; 544/353
[58] Field of Search ......... 260/250 Q, 250 QN, 243.3; 544/353, 116, 62; 424/250; 426/532

[56] References Cited

U.S. PATENT DOCUMENTS 3,371,090  12/1968  Johnston ...................... 260/250 QN
3,555,025  1/1971   Ley et al. .................... 260/250 QN Primary Examiner—Mark L. Berch
Attorney, Agent, or Firm—Steinberg & Raskin

[57] ABSTRACT

The present invention deals with derivatives of quinoxaline-1,4-dioxides, processes for their preparation and their utility, inter alia, as pharmaceutical compositions for the treatment of infectious diseases as well as their use as antiseptic agents. Moreover said compounds show a good growth promoting effect in animals.

24 Claims, No Drawings

DERIVATIVES OF QUINOXALINE-1,4-DIOXIDES

The present invention relates to novel derivatives of quinoxaline-1,4-dioxides, to processes for their preparation and to pharmaceutical compositions comprising same.

The present invention consists in derivatives of quinoxaline-1,4-dioxide of general formula I

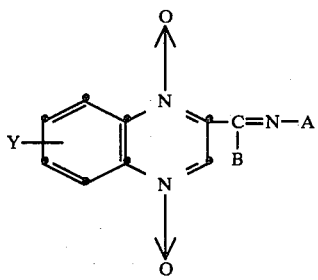

in which Y stands for at least one hydrogen or halogen atom, or a straight or branched alkyl and alkoxy radical;

A stands for a hydroxy group and then B stands either for chlorine;

for OR', R' standing for straight or branched alkyl radical;

or for NR"R''', R" and R''' standing for the same or different hydrogen; straight, branched or cyclo-alkyl radical; hydroxy alkyl, substituted amino or alkoxyalkyl radical; an arylalkyl radical in which the aryl is optionally substituted by one or more alkyl, alkoxy or thiotrifluoromethyl radical or by a halogen atom; or for a radical NHD, D standing for

Z' standing for an O or S atom or for the NH radical and E standing for an alkyl or amino radical, or for O-Alk, Alk standing for an alkyl radical; a morpholine, oxazolidanyl and piperazino radical optionally substituted by an alkyl radical; and R" and R''' together with the N atom may form a heterocyclic ring in which R" and R''' together stand for one of the following radicals:

$(CH_2)_n$, n standing for an integer from 4 to 7, $(CH_2)_2-X-(CH_2)_2$, X standing for a O or S atom or for $NR^{iv}$, $R^{iv}$ standing for hydrogen or for an alkyl or alkoxy radical, $(CH_2)_2-N(Z)-(CH_2)_2$, Z standing for hydrogen or a straight or branched alkyl radical or for a hydroxy or alkoxy (straight or branched) alkyl radical or for an alkoxy adduct; in case that R" and/or R''' stand for hydroxy the tautomers thereof; and in case that B stands for a chlorine atom A may stand also for OOC—R R standing for branched or straight-alkyl or halogen substituted alkyl radical or a phenyl radical optionally substituted by one or more nitro groups.

The compounds according to the present invention show good antimicrobial, in particular antibacterial properties, as do some other known quinoline dioxides. Their spectrum of activity comprises both gram positive and gram negative bacteria. Some of the compounds according to the present invention were, as is shown in the following Tables, active against systemic infections in mice caused by E.Coli and Staph.aur. and also in experimental urinary tract infections caused by E.Coli in mice. The compounds according to the present invention are also active against various pathogenic fungi which is not the case with the known compounds. The new compounds may thus be utilised, inter alia, as antiseptic and anti-infection agents. They can also be utilised as agents for the control of chronic respiratory diseases in fowl.

Moreover, the compounds according to the present invention showed a good growth promoting effect in animals studies. Thus for some compounds 6–18% increase in growth promotion was measured with no undesired side-effects. The compounds can thus also be utilised in order to improve the efficient feeding of cold and warm-blooded animals.

The toxicity of the compounds tested is relatively low. The $LD_{50}$ varied between 1.5 g/kg to 4.5 g/kg. Some of the compounds were also non-mutagenic is host mediated assay. This toxicity is much lower than that of other commercially available quinoxaline dioxides.

Some of the compounds of general formula I, namely those indicated hereinafter as Ia are also valuable starting materials for the preparation of other compounds of general formula I.

The antimicrobial activity of some compounds according to the present invention was measured and the results are shown in the following Tables. The activity is indicated as the minimal inhibitory concentration in $\mu g/ml$.

The activity of compounds of the following formulae are listed in the Tables:

Table I

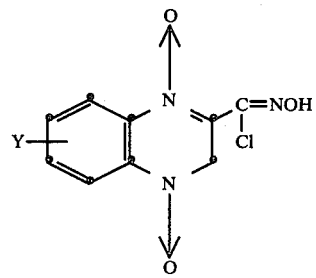

Ia

Table II

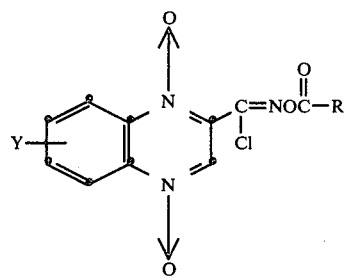

Ib

Table III

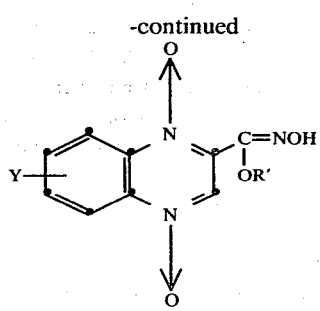

Ic

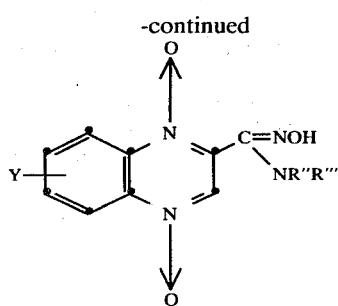

Id

In all listed compounds Y stands for hydrogen

In all listed compounds Y stands for hydrogen

TABLE I

| Y | Staph. Aur. | B. Cereus | B. Subtilis | Shig. Flex | Salm. Typh. | E. Coli | Cand. Alb. | Trichophyt. Rubrum | Cript. Neof. | Mycoplasma gallisept |
|---|---|---|---|---|---|---|---|---|---|---|
| H | 25 | 25 | 11-100 | 11-100 | 25 | 25 | | 11-100 | | 25-50 |
| $CH_3$ | 25 | 25 | 11-100 | 11-100 | 50 | 25 | 25 | 25 | 50 | |
| Cl | 25 | 10 | 11-100 | 11-100 | 25 | 25 | | 11-100 | | 10-25 |
| 6.7 $CH_3$ | 11-100 | 11-100 | >100 | >100 | >100 | >100 | | 11-100 | | |

TABLE II

| Y | R | Staph. Aur. | B. Cereus | B. Subtilis | Shig. Flex. | Salm. Typh. | E. Coli | Cand. Alb. | Trichophyt. | Cript. Neof. | Mycoplasma gallisept |
|---|---|---|---|---|---|---|---|---|---|---|---|
| Cl | $CH_2CH_3$ | 11-100 | | 11-100 | | | | 1 | 1 | 1 | |
| Cl | $CH_3$ | 11-100 | | 11-100 | 11-100 | | | 1 | 2 | 2 | |
| $CH_3$ | $CH_3$ | | | 11-100 | 11-100 | | | 10 | 1 | 10 | |
| H | $CH_2Cl$ | 20 | 25 | 11-100 | 11-100 | 50 | 25 | | 11-100 | | 25 |
| H | $p\text{-}NO_2\text{-}C_6H_5$ | | | | 11-100 | 11-100 | | | 11-100 | | 50 |
| H | $CH_2CH_3$ | 10 | 25 | 11-100 | 11-100 | 25 | 25 | | | | |

TABLE III

| R' | Staph. Aur. | B. Cereus | B. Subtilis | Shig. Flex. | Salm. | E. Coli | Mycoplasma |
|---|---|---|---|---|---|---|---|
| $CH_3$ | 10 | 10 | 11-100 | 11-100 | 10 | 10 | 2-10 |
| $C_2H_5$ | 10 | | 11-100 | 11-100 | 11-100 | 11-100 | |

TABLE IV

| R" | R'" | Staph. Aur. | B. Cereus | B. Subtilis | Salm. Typh. | E. Coli | Proteus | Pseud. Aur. | Cand. Alb. | Trichophyt. Rubrum | Aspergillus Niger | Cript. Neof. | Mycoplasma sept |
|---|---|---|---|---|---|---|---|---|---|---|---|---|---|
| H | $C_4H_3$ | 11-100 | | 11-100 | | | | | | 10 | | | |
| H | −N⌒O (morpholino) | 11-100 | | 11-100 | | | | | | 1 | | | |
| H | $NHCOCH_3$ | 10 | 11-100 | | 11-100 | 11-100 | 11-100 | | | 11-100 | | | |
| $C_2H_5$ | $C_2H_5$ | 11-100 | 11-100 | | 50 | 50 | | 10 | | | | | |
| H | $CH_2CH_2CH_3$ | 10 | 25 | 25 | 25 | 11-100 | 10 | | 11-100 | 11-100 | 11-100 | 11-100 | 25-50 |
| H | $CH_2CH_3$ | 10 | 25 | 25 | 25 | 11-100 | | | | | | | 10-25 |
| H | $CH_3$ | 10 | 25 | 25 | 25 | 11-100 | | | | | | | 10-20 |
| | N−$CH_3$ (N-methylpiperazino) | 25 | 25 | 25 | 25 | 11-100 | 11-100 | | | | | | 10 |
| $CH_3$ | $CH_3$ | 10 | 50 | 10 | 10 | | | | | | | | |
| H | −N⌒N−$CH_3$ | 50 | 50 | | 25 | 25 | 11-100 | 11-100 | 25 | 25 | | 10-25 | 2 |
| H | $NHCO_2C_2H_5$ | 10 | | 10 | 10-25 | 40-50 | | | | | | | 10-25 |
| H | $N(CH_3)_2$ | 10-25 | 10 | | 100 | 2-10 | | | | | | | 25 |

Some compounds of general formula Id were tested also in vivo. The results are shown in Table V.
In the column protection:
+ indicates protection >80%

+/— indicates protection 50–80%
— indicates protection <50%

TABLE V

| Y | R₁ | R₂ | Systemic *E. Coli* infection in mice | | Systemic *St. aur* infection in mice | | U. Tract infections in mice (*E. Coli*) | | *E. Coli* infections in chick | | U. Tract infections in mice (proteus) | |
|---|---|---|---|---|---|---|---|---|---|---|---|---|
| | | | Protection | Dosage | Protection | Dosage | Protection | Dosage | Protection | Dosage | Protection | Dosage |
| H | H | CH₃ | + | 2,5 mg × 2 per day | + | 2,5 mg × 2 per day | | | + | 50 mg/kg | | |
| H | H | C₂H₅ | + | 2,5 mg × 2 per day | +/− | 2,5 mg × 2 per day | | | | | | |
| H | H | C₃H₇ | + | 2,5 mg × 2 per day | − | 5 mg × 2 per day | + | 2,5 mg × 10 days | | | | |
| H | CH₃ | CH₃ | + | 2,5 mg × 2 per day | +/− | 2,5 mg × 2 per day | + | 2,5 mg × 10 per days | + | 50 mg/kg | | |
| H | —N⌒O (morpholino) | H | + | 2,5 mg × 2 per day | + | 2,5 mg × 2 per day | | | − | 50 mg/kg | | |
| H | —N⌒N—CH₃ (piperazinyl) | | + | 1,25 mg × 2 per day | +/− | 2,5 mg × 2 per day | + | 2,5 mg × 10 days | | | + | 2,5 mg × 10 days |
| H | —N⌒N—CH₃ (piperazinyl) | | + | 5 mg × 2 per day | | | + | 5 mg × 10 days | | | | |
| H | H | NHCOCH₃ | + | 2,5 mg × 2 per day | + | 2,5 mg × 2 per day | | | | | | |
| H | H | NHCOOC₂H₅ | + | 1,25 mg × 2 per day | + | 2,5 mg × 2 per day | + | 2,5 mg × 10 days | | | | |

The new compounds of general formula I may be administered per se, but are usually administered as the active part of a composition i.e., in the form of tablets, capsules, ampules, suppositories, suspensions or solutions. Said compositions are prepared in a conventional manner i.e, by addition of a suitable pharmaceutically acceptable binder, extender, carrier, emulsifier, solvent, other suitable therapeutic compounds and the like.

Moreover, the new compounds of general formula I may also be utilised as feed additives, or may be part of a feed pre-mix. In such feed premix the active ingredient, namely the compound of general formula I is mixed with an inert diluent, for example kaolin, talc, calcium carbonate, fuller's earth, attapulgus clay or ground oyster shells, or is mixed with a nutrient diluent, for example whole ground corn, corn distiller's dry grain, wheat shorts or corn cob meal. Said premix is then diluted with a suitable foodstuff in order to provide a suitable medicated foodstuff which can be eaten directly by the animal, e.g. the fowl. In case that the foodstuff is to be fed to fowl it comprises preferably 0.001%–1%, advantageously 0.005–0.05%, by weight of the active ingredient. Concentrated premixes comprise 1–99% preferably 5–25% by weight of the active ingredient.

The present invention consists also in a process for the preparation of compounds of general formula I in which a compound of general formula II

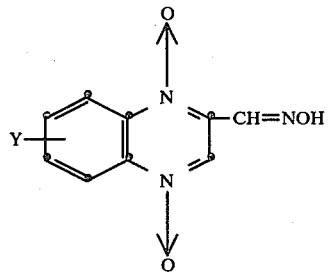

in which Y has the same meaning as above is chlorinated in a solvent to yield a compound of general formula Ia

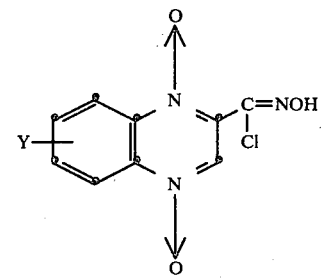

in which Y has the same meaning as above and, if desired, the compound of general formula I is reacted in a suitable solvent either a. with a compound of general formula III (R—CO₂)O or R—CO—Cl to yield a compound of general formula Ib

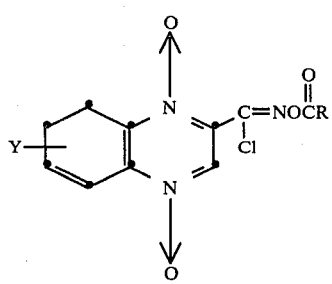

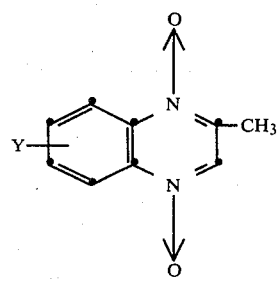

in which formulae Y and R have the same meanings as above;

b. with a compound of general formula IV

R'OT to yield a compound of general formula Ic

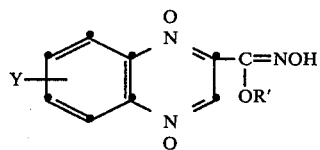

in which formulae Y and R' have the same meanings as above and T stands for an alkali metal, e.g. sodium; or c. with a compound of general formula V

HNR"R'"

to yield a compound of general formula Id

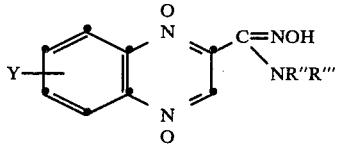

in which formulae Y, R" and R'" have the same meanings as above.

Suitable solvents are, for example, alcohols, e.g. methanol, ethanol, isopropanol. The conversion to compounds Ib, Ic and Id, respectively is performed at a temperature verying from room temperature to the boiling temperature of the solvent.

The compounds of general formula II are known. However the known processes for their preparation are not satisfactory. They usually consist in at least a two step process, which is cumbersome and complicated. Thus the present invention consist also in a process for the preparation of compounds of general formula II in which a compound of general formula VI is reacted with a suitable alkyl nitrite in a suitable solvent, under acidic conditions.

As suitable alkyl nitrite there may be mentioned for example, isoamylnitrite and butylnitrite.

As suitable solvent there should be mentioned dioxane. As acid there is preferably utilised HCl.

Compounds of general formula VI are known (see J.Chem. Soc. (1943) p. 322–5).

The invention will now be illustrated with reference to the following Examples without being limited by them.

All temperatures are given in degrees centigrade.

All melting points are uncorrected. The IR Spectra are measured in KBr pellets.

The numerals given are the main absorption lines indicated in microns.

The yields in brackets are percentage of the theoretical. The solvents in brackets after the m.p. are those from which the compound was recrystallised.

EXAMPLE 1

1.4 g of 2-methyl-quinoxaline-1,4 dioxide, 9 ml of dioxane and 1.5 ml of a 14% HCl dioxane solution were introduced into a 100 ml three necked flask. The solution was stirred and then 1 g of isoamylnitrite was added. The mixture was then refluxed for 2 hours. Then 1 g of isoamylnitrite and another 1.5 ml of the 14% HCl dioxane solution were added. The mixture was then heated for another hour, then cooled and the yellow precipitate obtained was filtered off to yield of 1.42 g (91%) of 2-carboxaldoxime-quinoxaline-1,4 dioxide; m.p. 239°–240° C.

I.R.: 6.5, 6.75, 7.25, 8.05, 9.12, 9.8, 12.25, 13.12

The compound was identical with one prepared according to the literature.

EXAMPLE 2

1.4 g of 2-methyl-quinoxaline-1,4-dioxide, 9 ml of dioxane and 1.5 ml of a 14% HCl dioxane solution were introduced into a 100 ml three necked flask. Mixing was started and then 1 g of butyl nitrite was added rapidly. The mixture was then heated for 75 minutes on a boiling water bath. The suspension obtained was cooled and the solid precipitate was filtered off to yield 1.55 g (95%) of 2-carboxaldoxine-quinoxaline-1,4 dioxane; m.p. 221°–222° C. The compound was identical with that of Example 1.

EXAMPLE 3

In a similar manner to that described in Example 2, 1.68 g of 2-methyl-7-chloro-quinoxaline-1,4-dioxide was treated with 10 ml of dioxane, 1.5 ml of a 14% HCl dioxane solution and 1 g of butyl nitrite to yield 1.8 g (94.5%) of 2-carboxaldoxine-7-chloro quinoxaline-1,4 dioxide; m.p. 236°–238° .

I.R.: 6.23, 6.5, 6.7, 7.3, 8.1, 8.5, 8.9, 9.7, 11.2, 11.8, 12.9

The compound was identical with one prepared according to the literature.

EXAMPLE 4

In a similar manner to that described in Example 2, 1.5 g of 2,6,7-trimethyl-quinoxaline-1,4-dioxide, was treated with 10 ml of dioxane and 1.5 ml of 14% HCl dioxane solution and 1 g of butyl nitrite. Refluxing was performed for three hours to yield 1.43 g (83%) of 2-carboxaldoxime-6,7-dimethyl-quinoxaline-1.4 dioxide; m.p. 221°–222°.

I.R.; 6.5, 6.55, 7.21, 7.35, 8.05, 8.56, 9.9, 11.25, 13.1

EXAMPLE 5

In a similar manner to that described in Example 2, 3 g of 2,7-dimethyl-quinoxaline-1,4-dioxide were treated with 18 ml of dioxane and 3 g of a 14% dioxane solution and 2 g of butyl nitrite. (Reflux time: 2 hours) to yield 3 g (86.5%) of 2 carboxaldoxime-7-methyl-quinoxaline-1,4-dioxide; m.p. 228.5°–233.5° (crude).

I.R.: 6.2, 6.7, 7.3, 8.05, 8.65, 9.7, 10.2, 11.95, 12.75, 13.25

EXAMPLE 6

1 g of 2-carboxaldoxime-quinoxaline-1,4-dioxide and 40 ml of dry methanol were introduced into a 4 necked 100 ml flask. The suspension obtained was cooled to 5°. A chlorine stream was then bubbled through said suspension which was kept the whole time at 5° to 10°. The introduction of chlorine was discontinued when the methanolic solution was saturated. The mixture was then stirred overnight at room temperature. The precipitate was filtered off and washed with methanol to yield 0.6 g (51:2%) of 2($\alpha$-chloro)-carboxaldoxime-quinoxaline-1,4-dioxide; m.p. 206.5°–207.5°. The analysis was calculated for $C_9H_6ClN_3O_3$ Calc.: C: 45.00%; H: 2.50%; N: 17.5%; Cl: 14.8%; Found: C: 45.10%; H: 2.60% N: 17.60% Cl: 14.54%

I.R.: 6.7, 6.8, 7.4, 8.15, 8.37, 9.23, 9.8, 11.47, 12.38, 12.9

EXAMPLE 7

In a similar manner to that described in Example 6, 1.5 g of 2-carboxaldoxime-7-methyl-quinoxaline-1,4-dioxide was treated with chlorine gas to yield 1.21 g (69.5%) of 2-($\alpha$-chloro)-carboxaldoxime-7-methyl-quinoxaline-1,4-dioxide; m.p. 208.5 (cellusolve). The analysis was calculated for $C_{10}H_8ClN_3O_3$ Calc.: C: 47.3%; H: 3.16%; N: 16.6%; O: 18.95%; Cl:14.01%; Found: C: 47.22%; H: 3.23%; N: 16.37%; O: 19.06%; Cl: 13.80%

I.R.: 6.25, 7.21, 7.35, 7.28, 2.45, 12.15

EXAMPLE 8

In a similar manner to that described in Example 6, 2.65 g of 2-carboxaldoxime-7-chloro-quinoxaline-1,4-dioxide was treated in methanol with gaseous chlorine to yield 1.27 g of 2-($\alpha$-chloro)-carboxaldoxime-7-chloro-quinoxaline-1,4-dioxide; m.p. 196°–197°.

I.R.: 6.2, 6.5, 6.7, 6.9, 7.35, 8.25, 8.95, 9.7, 11.15, 11.25, 11.75, 12.25

EXAMPLE 9

In a similar manner to that described in Example 6, 1 g of 2-carboxaldoxime-6,7-dimethyl-quinoxaline-1,4-dioxide, was treated in methanol with gaseous chlorine, to yield 0.67 g (75.5%) of 2-($\alpha$-chloro)-carboxaldoxime-6.7-dimethyl-quinoxaline-1,4-dioxide; m.p. 204°–206° (ethoxy ethanol).

I.R.: 3.75, 7.32, 8.6, 8.8, 11.3, 12.15,

EXAMPLE 10

A mixture of 1 g of 2-($\alpha$-chloro)-carboxaldoxime-7-chloro-quinoxaline-1,4-dioxide and 10 ml of propionic acid anhydride was refluxed for 1 hour. The solvent was then distilled off in vacuum and the oily residue obtained was triturated with propanol recrystallization in succession from isopropanol and from ethoxy ethanol to yield 0.6 g of 2-($\alpha$-chloro-0-propionyl)-carboxaldoxime-7-chloro-quinoxaline-1,4-dioxide; m.p. 211°–212°. The analysis was calculated for $C_{12}H_{10}Cl_2N_3O_4$ Calc.: C: 43.5%; H: 3.02%; Cl: 21.43%; N: 12.7%; O: 19.35%; Found: C: 43.72%; H: 2.79%; Cl: 21.33%; N: 12.79%; O: 19.26%

I.R.: 5.52, 6.2, 7.25, 8.13, 8.51, 9.05, 9.42, 11.2, 11.3, 12.25

EXAMPLE 11

A mixture of 1 g of 2-($\alpha$-chloro)-carboxaldoxime-7-chloro-quinoxaline-1,4-dioxide and 20 ml of acetic acid anhydride was refluxed for 1 hour. The solvent was then distilled off in vacuo, and the residue was triturated with isopropanol. The solid formed was filtered off. Recrystallization from dioxane and nitromethane gave 0.6 g of 2-[$\alpha$-chloro-(0-acetyl)-carboxaldoxime]-7-chloro-quinoxaline-1,4-dioxide; m.p. 234°–235°. The analysis was calculated for $C_{11}H_7Cl_2N_3O_4$ Calcl.: C: 41.4%; H: 2.22%; Cl: 22.5%; N: 13.3%; O: 20.2%; Found: C: 41.93%; H: 2.27%; Cl: 22.25%; N: 13.45%; O: 20.07%

I.R.: 5.55, 7.3, 8.15, 8.5, 9.9, 10.53, 11.6, 12.28

EXAMPLE 12

A mixture of 0.5 g of 2-($\alpha$-chloro)-carboxaldoxime-7-methyl-quinoxaline-1,4-dioxide, and 10 ml of acetic anhydride was heated at 140° for 3 hours. The solvent was then distilled off in vacuo, and the residue was triturated with methanol. The solid formed was filtered off. Recrystallization in succession from nitromethane and from isopropanol yielded an analytical sample of 2-[$\alpha$-chloro-(0-acetyl)-7-methyl-quinoxaline]-1,4-dioxide; m.p. 216.5°–217.5°. The analysis was calculated for $C_{12}H_{10}ClN_3O_4$ Calcl.: C: 43.70%; H: 3.38%; Cl: 12.0%; N: 14.20%; O: 21.70%; Found: C: 48.78%; H: 3.33%; Cl: 11.78%; N: 14.04%; O: 21.81%

I.R.: 5.55, 6.12, 7.3, 8.5, 9.9, 10.55, 11.25, 12.21

EXAMPLE 13

1.2 g of 2-($\alpha$-chloro)-carboxaldoxime-quinoxaline-1,4-dioxide, 30 ml of dry benzene and 0.5 ml of triethylamine were introduced into a 100 ml flask equipped with an efficient stirrer and reflux condenser. Stirring was started and the mixture was cooled in an ice bath. 0.79 g of chloroacetyl chloride was then slowly added and the mixture was stirred in the cold for one hour. It was then left overnight and thereafter refluxed for 5 hours. The precipitated solids were filtered off and washed with benzene. Crystallization from ethoxy ethanol yielded 2-[$\alpha$-chloro-(0-chloroacetylcarboxaldoxime)]-quinoxaline-1,4-dioxide; m.p. 191°–193°. The analysis was calculated for $C_{11}H_7Cl_2N_3O_4$ Calc.: C: 41.80%; H: 2.22%; N: 13.30%; O: 20.25%; Found: C: 41.76%; H: 2.26%; N: 13.10%; O: 20.00%

I.R.: 5.55, 7.27, 8.15, 9.02, 10.17, 11.5, 11.8, 12.2, 12.7

EXAMPLE 14

0.265 g of sodium carbonate was suspended in 50 ml of acetone. 1.2 g of 2-(α-chloro)-carboxaldoxime-quinoxaline-1,4-dioxide was added to the suspension. The mixture was cooled to 0° and 0.925 g of p-nitrobenzoyl chloride was added in small portions. The mixture was then stirred for several hours at room temperature. The solids obtained were filtered off and washed with acetone. Several crystallizations from ethoxy ethanol yielded 2-[α-chloro-(0-p-nitrobenzyl)-carboxaldoxime]-quinoxaline-1,4-dioxide; m.p. 244°. The analysis was calculated for $C_{16}H_9ClN_4O_6$ Calc.: C: 49.40%; H: 2.32%; Cl: 9.13%; N: 14.40%; O: 24.70%; Found: C: 49.27%; H: 2.21%; Cl: 9.16%; N: 14.48%; O: 24.66%

I.R.: 5.67, 6.25, 6.58, 7.32, 8.1, 8.21, 9.75, 9.95, 11.42, 12.3, 12.87, 14.05

EXAMPLE 15

In a similar manner to that described in Example 10, 2-[α-chloro-(0-acetyl)-carboxaldoxime-quinoxaline-1,4-dioxide was prepared; m.p. 191.5°–193° (cellosolve). The analysis was calculated for $C_{12}H_{11}ClN_3O_4$ Calc.: C: 48.5%; H: 3.70%; Cl: 11.95%; N: 14.18%; O: 21.50%; Found: C: 48.6%; H: 3.36%; Cl: 12.17%; N: 14.01%; O: 21.54%

I.R.: 5.6, 7.4, 8.2, 9.05, 9.4, 10.05, 10.55, 11.25, 11.5, 12.35, 12.85

EXAMPLE 16

In a similar manner to that described in Example 11 the 0-acetyl derivative of 2-[α-chloro-(0-acetyl)-carboxaldoxime]-6,7-dimethyl-quinoxaline-1,4-dioxide was prepared, m.p. 219.5°–220°5. The analysis was calculated for $C_{13}H_{12}Cl\,N_3O_4$ Calc.: C: 50.20%; H: 4.06%; Cl: 11.42%; N: 13.75%; O: 20.09%; Found: C: 50.27%; H: 4.07%; Cl: 11.33%; N: 13.62%; O: 20.49%

I.R.: 5.62, 7.38, 8.55, 10.00, 10.65, 11.22, 12.28

EXAMPLE 17

50 ml of absolute methanol and 0.11 g of metallic sodium were put into a 100 ml flask equipped with an efficient stirrer moisture tight condenser and thermometer. After all the sodium was dissolved 0.6 g of 2-(α-chloro)-carboxaldoxime-quinoxaline-1,4-dioxide was added thereto and the mixture obtained was stirred overnight at room temperature. The solution was then acidified with an alcoholic solution of hydrochloric acid. The crystals which precipitated were filtered off and recrystallized from ethoxy ethanol to yield 0.15 g of 2-(α-ethoxy)-carboxaldoxime-quinoxaline-1,4 dioxide; m.p. 212.5°–214.5°. The analysis was calculated for $C_{11}CH_{11}N_3O_4$ Calc.: C: 53.01%; H: 4.45%; N: 16.86%; O: 25.62%; Found: C: 52.99%; H: 4.25%; N: 16.72%; O: 25.50%;

I.R.: 5.60, 5.95, 7.20, 9.10, 10.50, 11.30, 12.85

The mother liquor was concentrated in vacuo to half of its volume; the crystals that precipitated were filtered off and recrystallized from ethoxy ethanol to yield 0.3 g of 2-(α-methoxy)-carboxaldoxime-quinoxaline-1,4-dioxide, m.p. 190°–193°. The analysis calculated for $C_{10}H_9N_3O_4$.

Calc.: C: 5.06%; H: 3.82%; N: 17.87%; O: 27.23%; Found: C: 50.98%; H: 3.68%; N: 18.15%; O: 27.00%

I.R.: 6.05, 6.62, 7.3, 8.2, 9.17, 10.1, 11.4, 11.85, 12.92, 13.1

EXAMPLE 18

0.40 g of 2-(α-chloro)-carboxaldoxime-quinoxaline-1,4-dioxide was suspended in 30 ml of anhydrous methanol. Ethylamine gas in large excess was then bubbled through the suspension obtained. The color of the crystals turned orange, and soon after they dissolved. The mixture was then stirred overnight at room temperature. The crystals that precipitated were filtered off, and washed with methanol. Recrystallization from isopropanol yielded 0.3 g of 2-(N-ethyl amino)-carboxamidoxime-quinoxaline-1,4-dioxide; m.p. 193°–194°. The analysis was calculated for $C_{11}H_{12}N_3O_4$ Calc.: C: 52.22%; H: 4.87%; N: 22.57%; O: 19.34% Found: C: 51.88%; H: 4.52%; N: 22.21%; O: 19.27%

I.R.: 6.15, 7.32, 8.15, 8.32, 9.2, 9.6, 9.7, 10.5, 11.8, 12.2, 12.75

In a manner similar to that described above there was prepared 2-(N-methylamino)-carboxaldoxime-quinoxaline-1,4-dioxide; m.p. 193°–195°.

I.R.: 6.10, 8.30, 9.2, 10.6, 12.75

EXAMPLE 19

1.2 g of 2-(α-chloro)-carboxaldoxime-quinoxaline-1,4-dioxide was suspended in 50 ml of methanol and 1.5 g of α-butylamine was then added to the suspension. A light exothermic reaction was observed and the color of the suspended product turned from yellow to orange. The mixture was stirred overnight at room temperature and then the crystals obtained were filtered off and washed with methanol. The recrystallizations from nitromethane yielded 1.01 g of 2-(N-butylamino)-carboxamidoxime-quinoxaline-1,4-dioxide, m.p. 78°–9°. The analysis was calculated for $C_{13}H_{16}N_4O_3$ Calc.: C: 56.51%; H: 5.84%; N: 22.28%; O: 17.37% Found: C: 56.49%; H: 5.78%; N: 20.11%; O: 17.53%

I.R.: 3.1, 3.4, 6.05, 7.1, 7.45, 8.09, 9.15, 10.05, 11.32, 12.35

EXAMPLE 20

In a manner similar to that described in Example 18, 1.18 g of propylamine was reacted with 2.4 g of 2-(α-chloro)-carboxaldoxime-quinoxaline-1,4-dioxide to yield 2.2 g of 2-(propylamino)-carboxamidoxime-quinoxaline-1,4-dioxide; m.p. 180°–181°.

I.R.; 3.1, 6.1, 6.15, 7.27, 9.1, 10.17, 11.75, 12.22, 12.85

EXAMPLE 21

In a manner similar to that described in Example 20 there were prepared:

a. 2-(N-isopropylamino)-carboxaldoxime-quinoxaline-1,4-dioxide; m.p. 170°–171°
I.R.: 6.1, 7.85, 8.1, 9.2, 11.85, 12.92, 13.31
b. 2-[N-(2'-ethoxyethyl)-amino]-carboxaldoxime-quinoxaline-1,4-dioxide; m.p. 157°–158°
I.R.: 6.09, 7.41, 8.1, 9.15, 10.5, 11.47, 12.9, 13.2
c. 2-[N-(2'-diethylamino-ethyl)-amino]-carboxaldoxime-quinoxaline-1,4-dioxide; m.p. 157°–158°
I.R.: 8.08, 7.1, 7.9, 9.15, 11.35, 12.85, 13.15
d. 2-(N-dodecylamino)-carboxaldoxime-quinoxaline-1,4-dioxide; m.p. 195°
I.R.: 6.25, 7.0, 7.55, 8.25, 9.3, 10.6, 11.85, 13.1
e. 2-(α-N-dimethyl-hydrazino)-carboxaldoxime-quinoxaline-1,4-dioxide; m.p. 131°–134°
I.R.: 6.09, 7.35, 8.15, 8.31, 9.17, 10.5, 11.85, 12.9, 13.9

EXAMPLE 22

0.48 g of 2-(α-chloro)-carboxaldoxime-quinoxaline-1,4-dioxide was suspended in 30 ml of methanol. 0.5 g of diethyl amine were added to the suspension and the mixture was stirred overnight at room temperature. The solid which precipitated was filtered off and recrystalized from ethanol and isopropanol to yield 0.25 g of 2-(N-diethylamino)-carboxaldoxime-quinoxaline-1,4-dioxide; m.p. 158°–9°. The analysis was calculated for $C_{13}H_{16}N_4O_3$ Calc.: C: 56.31%; H: 5.84%; N: 20.38%; O: 17.38%
Found: C: 56.67%; H: 5.75%; N: 20.29%; O: 17.37%
I.R.: 6.07, 6.75, 7.18, 7.90, 8.12, 11.10, 12.09, 12.85

EXAMPLE 23

In a manner similar to that described in Example 22 there were prepared:
a. 2-(N-diisopropylamino)-carboxaldoxime-quinoxaline-1,4-dioxide; m.p. 168°
I.R.: 6.12, 7.42, 9.2, 11.75, 12.92
b. 2-(N-diisobutylamino)-carboxaldoxime-quinoxaline-1,4-dioxide; m.p. 161°–163°
I.R.: 6.15, 7.32, 9.15, 10.3, 11.82, 12.9

EXAMPLE 24

4.8 g of 2-(α-chloro)-carboxaldoxime-quinoxaline-1,4-dioxide were suspended in 100 ml of methanol. 2 g of acetyl-hydrazine were then added in one portion and the mixture obtained was stirred for 3 days at room temperature. The mixture was then heated on a steam bath for 4 hours; the precipitating solids were filtered off and washed with methanol; recrystallization from ethoxy ethanol yielded 3.5 g of 2-N-(acetyl-hydrazino)-carboxaldoxime-quinoxaline-1,4-dioxide; m.p. 184(decomp.)
I.R.: 3.00, 3.25, 5.95, 6.05, 6.6, 7.25, 8.25, 9.05, 9.55, 10.2, 12.15, 12.75

EXAMPLE 25

1.2 g of 2-(α-chloro)-carboxaldoxime-quinoxaline-1,4-dioxide was suspended in 50 ml of dry methanol. 1.02 g of N-amino morpholine was then added to the suspension and the mixture obtained was stirred overnight at room temperature. The precipitated solids were filtered off and washed with methanol. Two crystallizations from nitromethane yielded 1.43 g of 2-(N-morpholinoamino)-carboxamidoxime-quinoxaline-1,4-dioxide; m.p. 152° (decomp.) The analysis was calculated for $C_{13}H_{15}N_5O_4$ Calc.: C: 51.15%; H: 4.95%; N:22.94%; O: 20.96%
Found: C: 5.07%; H: 5.10%; N: 22.20%; O: 20.57%
I.R.: 3.05, 6.07, 7.1, 7.3, 9.25, 10.4, 10.99, 11.37, 12.3, 12.55

Acute oral $LD_{50}$ in mice 1.24 g/kg
Acute oral $LD_{50}$ in chicks 428 mg/kg

EXAMPLE 26

0.26 g of 2-(α-chloro)-carboxaldoxime-7-chloro-quinoxaline-1,4-dioxide was suspended in 30 ml of methanol. 0.2 g of N-methyl piperazine was added to the suspension and the mixture was stirred overnight at room temperature. The solids obtained were filtered off and washed with methanol. Recrystallization from nitromethane yielded 0.16 g of 2-(4'-methyl-piperazino)-carboxaldoxime-7-chloro-quinoxaline-1,4-dioxide; m.p. 237°–238°. The analysis was calculated for $C_{14}H_{16}ClN_5O_3$ Calc.: C: 49.8%; H: 4.75%; N: 20.7%; O: 14.25%; Cl: 10.55%; Found: C: 49.46%; H: 5.17%; N: 20.44%; O: 14.31%; Cl: 10.42%
I.R.: 6.02, 7.05, 7.4, 8.12, 9.12, 10.9, 11.5, 12.85, 13.3

In a manner similar to that described above there were prepared:
a. 2-(4'-methyl-piperazino)-carboxaldoxime-quinoxaline-1,4-dioxide; m.p. 203.5°–204.5°
I.R.: 3.7, 6.1, 7.2, 7.4, 8.2, 10.15, 11.87, 12.8,
Acute oral $LD_{50}$ in mice 1.24 g/kg
Acute oral $LD_{50}$ in chicks 400 mg/kg
b. 2-(4'-β-hydroxymethyl-piperazino)-carboxaldoxime-quinoxaline-1,4-dioxide; m.p. 193.5°–194.5°
I.R.: 2.8, 3.2, 3.5, 6.1, 7.35, 8.72, 9.32, 10.07, 10.28, 11.82, 12.1, 12.83

EXAMPLE 27

0.27 g of 2-(α-chloro)-carboxaldoxime-7-chloro-quinoxaline-1,4-dioxide was suspended in 20 ml of methanol. 0.17 g of piperidine was added to the solution obtained and the mixture was stirred overnight at room temperature. The crystals obtained were filtered off and washed with methanol. Recrystallization from nitromethane gave 2-piperidino-carboxaldoxime-7-chloro-quinoxaline-1,4-dioxide; m.p. 194°–195°. The analysis was calculated for $C_{14}H_{15}Cl\ N_4O_6$ Calc.: C: 52.20%; H: 4.65%; N: 17.40%; O: 14.90%; Cl: 11.01%; Found: C: 51.96%; H: 4.04%; N: 17.21%; O: 15.08%; Cl: 10.88%
I.R.: 3.2, 3.4, 3.55, 7.4, 8.9, 10.32, 10.5, 12.11, 12.20, 12.3, 12.4

In the same manner as described above 2-(piperidino)-carboxaldoxime-quinoxaline-1,4-dioxide was prepared; m.p. 187.5°–188.5°
I.R.: 3.4, 3.52, 6.12, 7.32, 7.42, 8.1, 9.05, 10.07, 11.8, 12.2, 12.8

EXAMPLE 28

0.26 g of 2-(α-chloro)-carboxaldoxime-7-chloro-quinoxaline-1,4-dioxide, was suspended in 20 ml of methanol. 0.18 g of morpholine was added to the solution and the mixture was stirred overnight at room temperature. The precipitating crystals were filtered off and washed with methanol. Recrystallization from nitromethane gave 0.23 g of 2-(morpholino)-carboxaldoxime-7-chloro-quinoxaline-1,4-dioxide; m.p. 206.5°–207.5°. The analysis was calculated for $C_{13}H_{13}Cl\ N_4O_4$ Calc.: C: 48.10%; H: 4.00%; N: 17.25%; O: 19.70%; Cl: 10.95%; Found: C: 47.95%; H: 4.44%; N: 17.30%; O: 19.58%; CL: 10.74%
I.R.: 3.6, 6.25, 7.25, 7.30, 7.45, 8.1, 8.47, 8.95, 9.7, 11.2, 11.9, 12.3, 12.7

In the same manner as described above the following compound was prepared:
2-(morpholino)-carboxaldoxime-quinoxaline-1,4-dioxide; m.p. 214°–211°
I.R.: 3.5, 6.11, 7.2, 7.37, 8.1, 8.3, 8.9, 9.15, 10.15, 12.25

EXAMPLE 29

0.48 g of 2-(α-chloro)-carboxaldoxime-quinoxaline-1,4-dioxide was suspended in 30 ml of ethanol. 0.72 g of 3,4-dimethoxy-phenethylamine was added and the mixture was stirred overnight at room temperature. The precipitating solids were filtered off and washed with methanol. Recrystallization from methanol yielded 0.7 g of 2-(3′,4′-dimethoxy-phenetylamino)-carboxaldoxime-quinoxaline-1,4-dioxide; m.p. 181.5°–184.5° (crude)

I.R.: 3.4, 3.5, 6.05, 6.17, 6.55, 7.05, 7.3, 7.92, 8.1, 9.1, 9.72, 10.4, 11.7, 12.75

EXAMPLE 30

In the same manner as described in Example 24, 2-(α-chloro)-carboxaldoxime-quinoxaline-1,4-dioxide was heated with dimethylamine gas to yield 2-(dimethylamino)-carboxaldoxime-quinoxaline-1,4-dioxide; m.p. 154°.

I.R.: 3.5, 7.18, 7.4, 8.1, 8.4, 9.15, 9.25, 10.1, 11.77, 12.05, 12.85

EXAMPLE 31

0.35 g of piperazine was dissolved in 10 ml of anhydrous methanol, 0.48 g of 2-(α-chloro)carboxaldoxime quinoxaline-1,4-dioxide was added in small portions during 1 hour to the solution. The reaction was performed with stirring overnight at room temperature. The precipitating solids were filtered off and washed with methanol and with boiling ethoxy ethanol. The product isolated was 0.33 g of 3-piperazino-carboxaldoxime-quinoxaline-1,4-dioxide CH$_3$OH; m.p. 188°–201°. The analysis was calculated for $C_{14}H_{15}N_5O_4$ Calcl.: C: 52.98; H: 4.76%; N: 22.07%; O: 20.18%; Found: C: 53.18%; H: 4.05%; N: 22.27%; O: 20.37%

I.R.: 2.99, 3.3, 3.55, 6.22, 6.3, 7.2, 7.42, 8.2, 8.78, 9.2, 10.1, 11.95, 12.17, 12.87

Treatment with an excess of piperazine yielded N,N′-di-(2-carboxaldoxime-quinoxaline-1,4-dioxide)-piperazine; m.p. 233°–5° (ethoxy ethanol).

EXAMPLE 32

1.2 g of 2-(α-chloro)-carboxaldoxime-quinoxaline-1,4-dioxide was suspended in 30 ml of anhydrous methanol. 1.08 g of diethanol amine was added to the suspension and the mixture was stirred for 3 days at room temperature. The solids precipitating were filtered off, washed and recrystallized from cellosolve to yield 2-(bis-β-hydroxy ethylamino)-carboxaldoxime-quinoxaline-1,4-dioxide; m.p. 174.5°–176.5°. The analysis was calculated for $C_{13}H_{18}N_4O_4$ Calc.: C: 50.32%; H: 5.85%; N: 18.05%; O: 25.78%; Found: C: 50.49%; H: 5.08%; N: 18.3%; O: 26.02%

I.R.: 3.01, 3.35, 6.25, 7.25, 7.4, 10.35, 11.3, 12.95

In a manner similar to that described above 0.13 g of ethanol amine was reacted with 0.24 g of 2-(α-chloro)-carboxaldoxime-quinoxaline-1,4-dioxide to yield 2-(β hydroxy-ethylamino)-carboxaldoxime-quinoxaline-1,4-dioxide; m.p. 178°–190°

I.R.: 3.0, 6.05, 8.2, 9.2, 11.9, 12.9

EXAMPLE 33

0.4 g of 1-amino-4-methyl-piperazine dihydrochloride hydrate was dissolved in 20 ml of methanol. 0.156 g of NaOH and 0.24 g of 2-(α-chloro)-carboxaldoxime-quinoxaline-1,4-dioxide were added in succession to the solution. The mixture then was stirred overnight at room temperature, then acidified with diluted hydrochloric acid and the precipitate obtained was filtered off washed and recrystallized twice from ethoxy ethanol. The product was isolated as the dihydrochloride hydrate of 2-(4′-methyl-piperazino)-carboxaldoxime-quinoxaline-1,4-dioxide; m.p. 194°–196°. The analysis was calculated for $C_{13}H_{12}Cl_2N_6O_6$ Calcl.: C: 46.50%; H: 2.44%; N: 17.10%; O: 19.50%; Cl: 14.45%; Found: C: 46.29%; H: 2.52%; N: 16.99%; O: 19.74%; Cl; 14.49%

I.R.: 3.2, 3.7, 6.2, 6.6, 7.3, 8.0, 8.9, 8.4, 9.07, 9.15, 9.6, 11.35, 12.2, 12.8

EXAMPLE 34

0.48 g of 2-(α-chloro)-carboxaldoxime-quinoxaline-1,4-dioxide and 0.54 g of aminoquanidine carbonate were placed in 50 ml of isopropyl alcohol and the mixture obtained was refluxed for 3 hours. The solids thus formed were filtered off, washed with hot ethoxy ethanol and dried in the air, to yield 0.17 g (21%) of 2-(1′-aminoguanidine)carboxaldoxime-quinoxaline-1,4-dioxide; m.p. 280°

I.R.: 2.9, 3.3, 3.6, 6.05, 7.35, 8.25, 9.2, 11.3, 12.15, 13.85

EXAMPLE 35

1.2 g of 2-(α-chloro)-carboxaldoxime-quinoxaline-1,4-dioxide and 1.04 g of ethyl carbazate were suspended in 50 ml of isopropylalcohol and the mixture was stirred and refluxed for 5 hours. The mixture was then cooled and the solids obtained were filtered off to yield 1.26 g (84%) of 2-(carbazinic acid ethyl ester)-carboxaldoxime-quinoxaline-1,4-dioxide; m.p. 189°–190° (cellosolve).

I.R.: 5.87, 6.15, 6.7, 7.25, 7.4, 7.95, 8.15, 10.25, 11.85, 13.05

Acute Oral LD$_{50}$ in mice 4.95 g/kg
Acute Oral in chicks 1.5g/kg

EXAMPLE 36

1.2 g of 2-(α-chloro)-carboxaldoxime-quinoxaline-1,4-dioxide and 0.93 g of aniline were refluxed overnight in 50 ml of isopropanol. The mixture was then cooled and the solids obtained were filtered off. Recrystallization from a isopropanol-ethanol mixture yielded 1.22 g (81.5%) of 2-(phenylamino)-carboxaldoxime-quinoxaline-1,4-dioxide; m.p. 186.5°–187.5°

I.R.: 6.1, 6.25, 6.7, 7.08, 7.18, 7.4, 8.1, 9.2, 10.5, 10.65, 11.12, 11.82, 12.95, 13.17, 13.35

EXAMPLE 37

1.2 g of 2-(α-chloro)-carboxaldoxime-quinoxaline-1,4-dioxide and 1.93 g of trifluoromethylthioaniline were introduced into 50 ml of isopropanol and the mixture was then refluxed for 6 hours. The mixture was cooled and the solids obtained filtered off, to yield 1 g (75%) of 2-(3′-trifluoromethylthiophenylamino)carboxaldoxime-quinoxaline-1,4-dioxide; m.p. 176°–177°

I.R.: 6.2, 6.35, 6.75, 7.25, 7.45, 8.2, 8.3, 9.0, 9.32, 9.75, 10.47, 11.92, 12.9

EXAMPLE 38

0.4 g of 2-(α-chloro)-carboxaldoxime-quinoxaline-1,4-dioxide and 0.52 g of 3,4-dimethoxyaniline were refluxed for 5 hours in 50 ml of isopropanol. The mixture was cooled and the solids obtained were filtered off, washed with isopropanol and dried in the air to yield 0.5 g (84%) of 2-(3′,4′-dimethoxy phenylamino)-carboxaldoxime-quinoxaline-1,4-dioxide; m.p. 190°–191°.

I.R.: 6.0, 6.1, 6.7, 8.1, 9.8, 11.8, 13.9

EXAMPLE 39

1.2 g of 2-(α-chloro)-carboxaldoxime-quinoxaline-1,4-dioxide and 1.27 g of p-chloroaniline were suspended in 50 ml of isopropanol and stirred and refluxed for 2 hours. The mixture was cooled and the solids precipitating were filtered off and washed with isopropanol. Crystallization from ethoxy ethanol yielded 1.5 g of 2-(p-chlorophenylamino)-carboxaldoxime-quinoxaline-1,4-dioxide; m.p. 207.5°–209°.

I.R.: 6.17, 6.28, 6.72, 7.2, 7.37, 8.1, 9.16, 10.37, 11.81, 12.08, 12.85

EXAMPLE 40

1.2 g of 2-(α-chloro)-carboxaldoxime-quinoxaline-1,4-dioxide, 1.11 g of semicarbazide hydrochloride and 0.84 g of sodium bicarbonate were suspended in 50 ml of isopropanol and the mixture was stirred and refluxed for 4 hours. The mixture was cooled and the solids obtained filtered off, washed several times with water and then with boiling ethoxy ethanol to yield 1.15 g of N-(α-(3-carboxaldoxime-quinoxaline-1,4-dioxide)-semicarbazide m.p. 191.5°

I.R.: 2.9, 6.05, 6.3, 9.15, 10.35, 11.95

EXAMPLE 41

0.48 g of 2-(α-chloro)-carboxaldoxime-quinoxaline-1,4-dioxide was suspended in 50 ml of methanol, 0.4 g of cyclohexyl amine was added and the mixture was stirred overnight at room temperature. The solids obtained were filtered off and dried. Recrystallization from nitromethane yielded 0.4 g of (80%) of 2-(N-cyclohexyl)-amino)-carboxaldoxime-quinoxaline-1,4-dioxide; m.p. 199°–199.5°

I.R.: 6.15, 6.27, 7.23, 7.35, 7.7, 9.2, 10.55, 11.05, 12.9, 12.07

EXAMPLE 42

0.48 g of 2-(α-chloro)-carboxaldoxime-quinoxaline-1,4-dioxide was suspended in 50 ml of methanol, 2 ml of a 40% solution of aminoxazolidone in methanol was added and the mixture was stirred overnight at room temperature. The solids obtained were filtered off and recrystallized from ethoxy-ethanol to yield 0.27% of 1-(3-carboxaldoime-quinoxaline-1,4 dioxide)-aminooxazolidone.

I.R.: 7.1, 7.4, 8.1, 9.0, 9.15, 9.78, 10.35, 11.82, 13.2

EXAMPLE 43

10 Parts of 2(ethoxy carbonylhydrazino)carboxaldoxime quinoxaline-1,4-dioxide and 90 parts of whole ground corn were thoroughly mixed in a blending machine. There was thus obtained a concentrated food premix which may be mixed in suitable proportions with an animal foodstuff, and the medicated foodstuff so obtained can be fed to poultry for the prophylactic control of coccidiosis.

The above process is repeated except that the whole ground corn is replaced by corn distillers dry grain, wheat shorts, corn cob meal, fuller's earth, calcium carbonate, attapulgus clay or ground oyster shells. There are likewise obtained concentrated food premixes which can be added in suitable proportions to animal foodstuffs thereby providing medicated foodstuffs which can be fed to poultry for the prophylactic control of coccidiosis.

EXAMPLE 44

In a growth promotion experiment that was conducted with male turkeys for 4 weeks utilizing 30, 50 and 75 g/ton of 2-(carbazamic acid ethyl ester)-carboxaldoxime-quinoxaline-1,4-dioxide in the feed, the increase in weight gain was 18.7%, 18.5% and 16% respectively. The results were statistically significant ($P<0.001$).

EXAMPLE 45

In a growth promotion experiment that was conducted with male turkeys for 4 weeks utilizing 50 g/ton of 2-(4'-methyl-piperazino)-carboxaldoxime-quinoxaline-1,4-dioxide in the feed, the increase in weight gain was 15.6%. The results were statistically significant ($P<0.001$).

EXAMPLE 46

Tablets are prepared comprising the following ingredients:

500 g of 2-(carbazinic acid ethyl ester)-carboxaldoximequinoxaline-1,4-dioxide
100 g Corn Starch
50 g cellulose
15 g magnesium stearate
10% starch paste The tablets are prepared as follows:

10% of starch paste is prepared and used for the granulation of the active principles. The granulate is passed through size 12 stainless steel screen and dried in a Colton oven for 8 hours. The dried granulate is passed through a 20 mesh stainless steel screen. Prescreened corn starch (60 mesh) and cellulose and magnesium stearate are added and the mixture blended in a tween cone blender for 10 minutes. The mixture is removed and compressed into tablets each weighing 670 mg using appropriate punches.

I claim:

1. A compound of the formula:

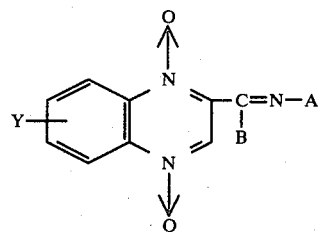

in which Y stands for at least one hydrogen or halogen atom, or a straight or branched chain lower alkyl or lower alkoxy;

A stands for hydroxy;

and B stands either for (a) chlorine, or for (b) OR', with R' standing for straight or branched chain lower alkyl, and when B stands for chlorine then A may stand also for OOC—R, with R standing for straight or branched chain alkyl or halogen substituted alkyl radical or phenyl or phenyl substituted by one or more nitro groups.

2. Compound according to claim 1 of the formula

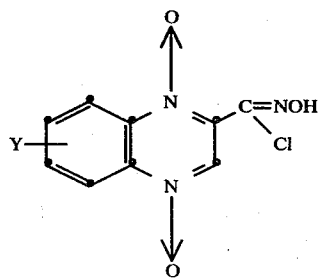

in which Y has the same meaning as in claim 1.

3. Compound according to claim 1 of the formula

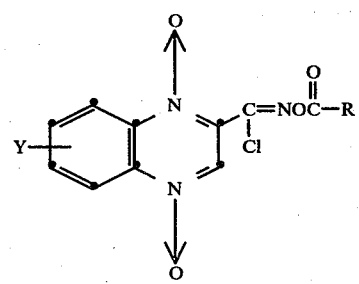

in which Y and R have the same meaning as in claim 1.

4. Compound according to claim 1 of the formula

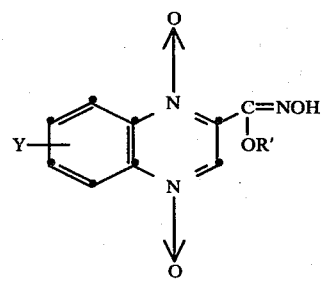

in which Y and R' have the same meaning as in claim 1.

5. Method for the promotion of the growth of animals which comprises administering a compatible carrier carrying a growth promoting effective amount of a compound of claim 1 to the animal.

6. Compound according to claim 1 being 2-(α-chloro)-carboxaldoxime-quinoxaline-1,4-dioxide.

7. Compound according to claim 1 being 2-(α-chloro)-carboxaldoxime-7-methyl-quinoxaline-1,4-dioxide.

8. Compound according to claim 1 being 2-(α-chloro)-carboxaldoxime-7-chloro-quinoxaline-1,4-dioxide.

9. Compound according to claim 1 being 2-(α-chloro)-carboxaldoxime-6,7-dimethyl-quinoxaline-1,4-dioxide.

10. Compound according to claim 1 being 2-(α-chloro)-O-propionyl-carboxaldoxime-7-chloro-quinoxaline-1,4-dioxide.

11. Compound according to claim 1 being 2-[α-chloro-(O-acetyl)-carboxaldoxime]-7-chloro-quinoxaline-1,4-dioxide.

12. Compound according to claim 1 being 2-[α-chloro-(O-acetyl)-7-methyl-quinoxaline]-1,4-dioxide.

13. Compound according to claim 1 being 2-[α-chloro-(O-chloroacetyl-carboxaldoxime)]-quinoxaline-1,4-dioxide.

14. Compound according to claim 1 being 2-[α-chloro-(O-p-nitrobenzoyl)-carboxaldoxime)]-quinoxaline-1,4-dioxide.

15. Compound according to claim 1 being 2-[α-chloro-(O-acetyl)-carboxaldoxime]-quinoxaline-1,4-dioxide.

16. Compound according to claim 1 being 2-[α-chloro-(O-acetyl)-carboxaldoxime]-6,7-dimethyl-quinoxaline-1,4-dioxide.

17. Compound according to claim 1 being 2-(α-ethoxy)-carboxaldoxime-quinoxaline-1,4-dioxide.

18. Compound according to claim 1 being 2-(α-methoxy)-carboxaldoxime-quinoxaline-1,4-dioxide.

19. Method for the treatement of infectious diseases which comprises administering to an animal requiring the same a compatible carrier carrying an effective amount of a compound of claim 1.

20. A pharmaceutical composition for infectious diseases or antiseptic purposes comprising a pharmaceutical carrier and a corresponding effective amount of a compound of claim 1.

21. A pharmaceutical composition according to claim 20, being in the form of tablets, capsules, ampules, suppositories, suspensions, or solutions.

22. A feed premix for animals comprising a carrier and a growth promoting effective amount of a compound of claim 1.

23. An animal feed including a growth promoting effective amount of a compound of claim 1.

24. The compound being 2-(x-carbazinic acid ethyl ester) - carboxaldoxime-quinoxaline-1,4-dioxide.

* * * * *